(12) United States Patent
Bhagwat et al.

(10) Patent No.: US 6,986,896 B2
(45) Date of Patent: *Jan. 17, 2006

(54) METHOD OF TREATING FUNGAL CONDITIONS OF THE SKIN

(75) Inventors: Dileep Bhagwat, Bronxville, NY (US); Bradley P. Glassman, Fairfield, NJ (US); Daniel Glassman, Fairfield, NJ (US)

(73) Assignee: Bradley Pharmaceuticals, Inc., Fairfield, NJ (US)

( * ) Notice: Subject to any disclaimer, the term of this patent is extended or adjusted under 35 U.S.C. 154(b) by 103 days.

This patent is subject to a terminal disclaimer.

(21) Appl. No.: 10/370,666

(22) Filed: Feb. 20, 2003

(65) Prior Publication Data

US 2003/0181526 A1 Sep. 25, 2003

Related U.S. Application Data

(63) Continuation-in-part of application No. 10/103,213, filed on Mar. 20, 2002, now Pat. No. 6,673,842.

(51) Int. Cl.
*A61K 6/00* (2006.01)
*A61K 7/00* (2006.01)
*A61K 31/17* (2006.01)

(52) U.S. Cl. .................. 424/401; 514/588; 514/922
(58) Field of Classification Search ............ 514/588, 514/922; 424/401
See application file for complete search history.

(56) References Cited

U.S. PATENT DOCUMENTS

| | | | |
|---|---|---|---|
| 4,295,567 A | 10/1981 | Knudsen | |
| 4,514,384 A | 4/1985 | Gallina | |
| 4,581,351 A | 4/1986 | Berke et al. | |
| 4,607,101 A | 8/1986 | Bernstein | |
| 5,334,326 A | 8/1994 | Bostick | |
| 5,340,836 A | 8/1994 | Reinhard et al. | |
| 5,407,958 A | 4/1995 | Heath et al. | |
| 5,445,823 A | 8/1995 | Hall et al. | |
| 5,525,635 A * | 6/1996 | Moberg | 514/588 |
| 5,573,765 A | 11/1996 | Reinhard et al. | |
| 5,632,996 A | 5/1997 | Ramirez et al. | |
| 5,645,428 A | 7/1997 | Yarborough | |
| 5,648,389 A | 7/1997 | Gans et al. | |
| 5,707,635 A | 1/1998 | Deckner et al. | |
| 5,843,998 A | 12/1998 | Song et al. | |
| 5,853,732 A | 12/1998 | Munden | |
| 5,899,878 A | 5/1999 | Glassman | |
| 5,919,470 A * | 7/1999 | Valdez et al. | 424/401 |
| 5,968,533 A | 10/1999 | Porter et al. | |
| 5,993,790 A * | 11/1999 | Strauss | 424/61 |
| 6,046,178 A | 4/2000 | Silvetti | |
| 6,262,117 B1 | 7/2001 | Sefton | |
| 6,281,239 B1 * | 8/2001 | Glassman | 514/399 |
| 6,380,236 B2 * | 4/2002 | Glassman | 514/399 |
| 6,429,231 B1 * | 8/2002 | Bhagwat et al. | 514/603 |
| 6,488,913 B2 | 12/2002 | Orlowski et al. | |
| 6,495,602 B1 | 12/2002 | Bhagwat et al. | |
| 6,573,301 B1 | 6/2003 | Glassman et al. | |
| 6,673,842 B2 * | 1/2004 | Bhagwat et al. | 514/588 |
| 6,743,417 B2 | 6/2004 | Glassman et al. | |
| 2003/0138466 A1 | 7/2003 | Bhagwat et al. | |
| 2003/0212127 A1 | 11/2003 | Glassman et al. | |

FOREIGN PATENT DOCUMENTS

| | | |
|---|---|---|
| WO | WO 96/19186 | 6/1996 |
| WO | WO-98/23152 | 6/1998 |

OTHER PUBLICATIONS

Aguado, C. et al., "Reaggregation and binding of cell wall proteins from Candida albicans to structural polysaccharides," *Research in Microbiology*, vol. 149, No. 5, pp. 327-338 (abstract) (1998).
Friedman-Bimbaum, R. et al., "Treatment of onychomycosis: A randomized, double-blind comparsion study with topical bifonazole-urea ointment alone and in combination with short-duration oral griseofulvin," *International Journal of Dermatology*, vol. 36 No. 1, p 67-69 (abstract) (1997).
Allerderm Laboratories, U-Lactin Lotion at http://www.allerderm.com.consumers/ulactin.asp Apr. 8, 2004.
Gennaro, A. et al., Remington's Pharmaceutical Science, 18th ed., pp. 767-768. (1990).
Gennaro, A. et al., Remington's Pharmaceutical Science, 18th ed., pp. 1305, 1310, 1317 and 1329 (1990).
Gloor, M., et al., "Do Urea/Ammonium Lacate Combinations Achieve Better Skin Protection and Hydration than Either Component Alone?", Skin Pharmacol. Appl. Skin Physiol., 15:35-43 (2002).
Lucy, J.A., "Functional and Structural Aspectes of Biological Membranes: A Suggested Structural Role for Vitamin E in the Control of Membrane Permeability and Stability", Annals of the New York Academy of Sciences, vol. 203, pp. 4-11 (Dec. 18, 1972).
Scharffetter-Kochanek, K., et al., "Photoaging of the Skin from Phenotype to Mechanism", Experimental Gerontology, vol. 35, No. 3, pp. 307-316 (May 2000).
Thiele, J., et al., "Antioxidant Network of the Stratum Corneum", Curr Probl Dermatol. Basel, Karger, vol. 29, pp. 26-42 (2001).

* cited by examiner

*Primary Examiner*—Vickie Kim
(74) *Attorney, Agent, or Firm*—Covington & Burling

(57) ABSTRACT

Methods of treating fungal conditions and onychomycosis are described which include administration of a safe and effective amount of urea in a topical formulation to an affected area on the skin or around a nail of a patient in need of treatment.

8 Claims, No Drawings

METHOD OF TREATING FUNGAL CONDITIONS OF THE SKIN

CROSS-REFERENCE TO RELATED APPLICATION

This is a continuation-in-part of application Ser. No. 10/103,213 of Mar. 20, 2002, now U.S. Pat. No. 6,673,842, for which benefit of priority is being claimed.

FIELD OF THE INVENTION

The present invention relates to methods of treating onychomycosis employing compositions with urea as the active ingredient. Onychomycosis refers to a fungal infection of the nail unit, defined as the nail matrix, bed or plate. The present invention also relates to the use of urea as an antifungal agent, and to methods of treating fungal conditions of the skin in humans with urea as a topical antifungal.

BACKGROUND OF THE INVENTION

Urea has been long recognized as a cosmetic ingredient in formulations acting as a humectant and moisturizer. High concentrations of urea, such as 40%, are also known to have mild, antibacterial effect. At these strengths the antibacterial effects are said to be similar to those of antibiotics, with the further advantage that all the common organisms are susceptible and the possibility of resistant strains need not be seriously considered. There have been reports of keratolytic activity attributed to urea with the ability at high concentrations to solubilize and denature protein. Dermatological compositions containing from 21 to 40 wt-% urea for treating dry scaly skin have been described in U.S. Pat. No. 5,919,470.

Concentrated solutions of urea can change the conformation of protein molecules. A striking effect is upon the water-binding capacity of the horny layer of the skin: pieces of normal horny layer, or scales from ichthyotic or psoriatic skin that have been soaked in 30% urea solution take up much more water. This is important because in maintaining the flexibility of the horny layer and the softness of the skin, the water content of the horny layer matters much more than its oil content.

Fungal infections of the nail are notoriously difficult to treat. Traditional, topical therapies cannot penetrate the nail plate, and eradicate the infection in and under the nail bed; they are useful only in milder forms of the disease. Systemic antifungal drug therapy is associated with potentially harmful side effects. Since oral antifungals are distributed throughout the entire body, systemic side effects such as elevated liver enzymes, gastrointestinal disorders and skin rashes are not uncommon and may require expensive medical intervention and laboratory tests.

Topical formulations for treating fungal infections, such as onychomycosis, have recently been described in U.S. Pat. No. 6,281,239B1. The method employs the use of a combination of a known antifungal agent and a tissue softening composition containing 30 to 60 wt-% urea.

We have now found that urea may be used as the sole active ingredient in treating fungal infections.

SUMMARY OF THE INVENTION

The present invention relates to methods of treating onychomycosis employing compositions containing urea as the antifungal agent. The present invention relates to methods for treating onychomycosis in humans with urea. These methods include topically administrating to the nail area of a human a safe and effective amount of urea. Onychomycosis refers to a fungal infection of the nail unit, defined as the nail matrix, bed or plate.

Accordingly, the present invention is a method for treating onychomycosis by topically administering a safe and effect amount of urea in a pharmaceutically acceptable carrier.

Another embodiment of the invention is a method of treating fungal conditions of the skin by topically administering to the affected area of the skin of a patient in need thereof a safe and effective amount of urea in a pharmaceutically acceptable carrier.

DETAILED DESCRIPTION OF THE INVENTION

The present invention is a method for treating or preventing onychomycosis. Such method includes administering to the nail area of a human in need of such treatment or prevention, a safe and effective amount of urea, for example, from about 10 to 60 wt-%, preferably about 30–50 wt-%, and particularly about 40 wt-%.

The present invention is a method for treating or preventing fungal conditions of the skin. Such method includes administering to the affected area of the skin of a human in need of such treatment or prevention, a safe and effective amount of urea, for example, from about 10 to 60 wt-%, preferably about 30–50 wt-%, and particularly about 40 wt-%.

The term "administering" as needed herein refers to any method which, in sound medical practice delivers the urea, e.g., 40% urea, to be treated in such a manner so as to be effective in the treatment of fungal conditions including, for example, onychomycosis. Preferably, the urea is administered topically in a single composition.

The phrase "safe and effective amount", as used herein, means an amount of urea sufficient enough to significantly and positively modify the condition to be treated but low enough to avoid serious side effects, within the scope of sound medical advice. The safe and effective amount of the urea of the present invention will vary with the particular condition being treated, the severity of the condition, the duration of treatment, the particular pharmaceutically acceptable carriers utilized, and the like factors within the knowledge and expertise of the attending physician.

The method of the present invention typically involves administering the urea in an amount to cover the affected area. The specific preferred quantity of the urea depends upon the nature of the fungus and other skin or nail conditions also present.

Thus for example, the dosing of the agents includes up to 720 days of administration of a pharmaceutical composition of the present invention.

For the method of the present invention, the duration of administration of the urea will vary according to the specific extent of the fungal condition being treated, but typically is within the range of 90 to 210 days.

Topical Antifungal Agents

Typically, a topical antifungal agent consists of known naturally-occurring, synthetic or semi-synthetic composition, or mixture thereof, which is safe for use in the methods of the present invention, and is effective in killing or substantially inhibiting the growth of fungi, including but not limited to dermatophytes or yeast, *Epidermophyton, Microsporum, Trichophyton* and *Candida albicans*, and others.

Antifungal agents known to be useful for the treatment of onychomycosis include but are not limited to: topical creams, ointments, solutions, lacquers and gels containing as active agents, for example, amoroline, betadine, bifonazole, butenafine, clotrimazole, econazole nitrate, isoconazole, ketoconazole, miconazole nitrate, naftifine hydrochloride, oxiconazole, sulfanazole, terbinafine, ticonazole, tolnaftate, undecenoates and ciclopirox. The above antifungal topical compositions are known to those skilled in the art.

We have now surprisingly found urea to be an antifungal agent of equal potency to known antifungal agents. Urea was previously known as mentioned in the above Background section for its effectiveness for tissue softening and treating dry skin, without the need of traditional preservatives. Although there may have been some belief that urea had a mild antibacterial effect, nothing would have suggested that urea was an effective antifungal agent.

Thus, the present invention provides a method of treating fungal conditions and onychomycosis in a topical composition containing urea as the sole active ingredient.

Another embodiment of the invention is the administration of another known topical antifungal agent as above described with a safe and effective amount of urea. In this aspect, the safe and effective amount of urea is typically administered either before, after or concomitantly with a safe and effective amount of a topical antifungal agent.

In addition to containing a therapeutically antifungal effective amount of urea, the composition includes a pharmaceutically acceptable carrier containing dermatologically acceptable excipients as described in U.S. Pat. No. 5,919,470, which patent is incorporated herein by reference. The excipients particularly include skin protectants which include a combination of semi-solid and liquid petroleum fractions. The semi-solid skin protectant is contained in about 5.5 to about 20 wt-% and includes petrolatum or a synthetic or semi-synthetic hydrocarbon of the same nature as petrolatum. Mixtures of such ingredients can also be used. The preferred semi-solid material is petrolatum, commercially available from a wide variety of sources.

The liquid portion skin protectant is a liquid petrolatum and contained in the composition in about 10 to about 20 wt-%. This material can include any synthetic or semi-synthetic oleaginous liquid fraction. A preferred embodiment is mineral oil, which is a liquid mixture of hydrocarbons obtained from petroleum.

Another preferred ingredient encompassed in the composition of the present invention is propylene glycol which may be contained up to about 5 wt-% in the composition, preferably in the range of from about 1 to about 5 wt-%.

Various compositions, e.g. creams, lotions, and gels, containing urea as the sole active ingredient at various concentrations were tested against *Trychophyton rubrum*, a fungus typically implicated in Moccasin tinea pedis and onychomycosis, and compared to traditional antifungal compositions. A solution of the individual or combination products were inoculated with a known starting concentration of *T. rubrum*. These solutions were then retested at the specific time intervals to determine the residual microbial content. The decrease in observed microbial content was measured by standard serial dilution methods.

The decrease in the residual microbial content calculated as a percentage of its initial starting concentration is the percent kill rate reported in the following table.

| PRODUCT(S) | "ACTIVE" INGREDIENT(S) | PERCENT KILL RATE AT TIME INDICATED | | | |
|---|---|---|---|---|---|
| | | 2 HRS | 6 HRS | 24 HRS | 3 DAYS |
| Carmol 40 Cream | 40% Urea | 93.6 | 99.5 | 98.2 | >99.9 |
| Loprox | 0.77% Ciclopirox | No kill | No kill | 91.0 | >99.9 |
| Loprox + Carmol 40 | 0.77% Ciclopirox + 40% Urea | 99.8 | >99.9 | >99.9 | >99.9 |
| Carmol 40 Cream | 40% Urea | Not tested | 99.9 | 99.9 | 99.9 |
| | 40% Urea | 62.1 | 93.0 | 91.7 | >99.9 |
| | 40% Urea | 99.7 | >99.9 | >99.9 | >99.9 |
| | 40% Urea | 97.6 | 98.3 | >99.9 | >99.9 |
| Carmol 40 Lotion | 40% Urea | 25.0 | 98.1 | 98.3 | >99.9 |
| Carmol 40 Gel | 40% Urea | 62.1 | 87.9 | >99.9 | >99.9 |
| Carmol 20 Cream | 20% Urea | 69.2 | 68.7 | 91.2 | >99.9 |
| Carmol 10 Lotion | 10% Urea | 80.4 | 82.1 | 83.3 | >99.9 |
| Carmol Scalp Lotion | 10% Sulfacetamide, 10% Urea | 78.3 | 82.9 | 98.0 | >99.9 |
| Miconazole | 2% Miconazole Nitrate | Not tested | >99.9 | >99.9 | >99.9 |
| Miconazole & Carmol 40 | 2% Miconazole + 40% Urea | Not tested | >99.9 | >99.9 | >99.9 |
| Nizoral | 2% Ketoconazole | 40.0 | No Kill | No Kill | 75.0 |
| Nizoral + Carmol 40 | 2% Ketoconazole + 40% Urea | 79.0 | 55.0 | 83.0 | 98.1 |
| Lotrimin | 1% Clotrimazole | 10.0 | No Kill | No Kill | No Kill |
| Lotrimin + Carmol 40 | 1% Clotrimazole + 40% Urea | 51.0 | 60.0 | 83.0 | >99.9 |
| Oxistat | 1% Oxiconazole | 88.0 | 96.0 | 99.0 | >99.9 |
| Oxistat + Carmol 40 | 1% Oxiconazole + 40% Urea | 99.5 | 97.0 | >99.9 | >99.9 |
| Mentax | 1% Butenafine | 99.6 | 99.9 | >99.9 | >99.9 |
| Mentax + Carmol 40 | 1% Butenafine + 40% Urea | 99.5 | 98.8 | >99.9 | >99.9 |
| Spectazol | 1% Econazole | No Kill | No Kill | 85.0 | >99.9 |
| Spectazol + Carmol 40 | 1% Econazole + 40% Urea | No Kill | 99.2 | 99.9 | >99.9 |

The above tests indicate that urea is an effective antifungal agent.

| Ingredient | Approximate Wt-% |
|---|---|
| urea | 40 |
| petrolatum or a synthetic or semi-synthetic hydrocarbon, or a semi-solid mixture thereof | 5.5–20 |
| liquid petrolatum or synthetic or semi-synthetic oleaginous liquid fraction, or a mixture thereof | 10–20 |
| $C_{16-18}$ aliphatic straight or branched chain fatty alcohol or fatty acid, or a mixture thereof | 0.25–2 |
| propylene glycol | 1–5 |
| glyceryl stearate | 1–3 |
| xanthan gum | 0.01–0.5 |
| water | balance |

Typical compositions employed in the present invention are for example:

| Ingredient | Approximate Wt-% |
|---|---|
| urea | 30 |
| petrolatum or a synthetic or semi-synthetic hydrocarbon, or a semi-solid mixture thereof | 5.5–20 |

-continued

| Ingredient | Approximate Wt-% |
|---|---|
| liquid petrolatum or a synthetic or semi-synthetic oleaginous liquid fraction, or a mixture thereof | 10–20 |
| $C_{16-18}$ aliphatic straight or branched chain fatty alcohol or fatty acid, or a mixture thereof | 0.25–2 |
| propylene glycol | 1–5 |
| glyceryl stearate | 1–3 |
| xanthan gum | 0.01–0.5 |
| mixture of a carbomer and triethanolamine | 0.05-30 |
| water | balance |

EXAMPLE

A typical formulation representing the particular and most preferred embodiment of the present invention is illustrated as follows and is manufactured by mixing the ingredients below using well known conventional methods:

| Ingredient | % W/W |
|---|---|
| Purified water | 36.149 |
| Urea USP | 40.000 |
| Carbopol 940 | 0.150 |
| Petrolatum | 5.940 |
| Mineral oil | 12.060 |
| Glyceryl stearate | 1.875 |
| Cetyl alcohol | 0.626 |
| Propylene glycol | 3.000 |
| Xanthan gum | 0.050 |
| Trolamine NF | 0.150 |
| TOTAL | 100.000 |

We claim:

1. A method of treating a fungal condition of the skin, wherein the fungal condition is *Tinea* pedis or is a condition caused by a dermatophyte, a *Trichophyton*, an *Epidermophyton*, and *Candida Albicans*, comprising:
   administering to an affected area of the skin of a patient a composition consisting essentially of urea as the sole active ingredient and a dermatologically acceptable excipient selected from the group consisting of petrolatum or a synthetic or semi-synthetic hydrocarbon, or a semi-solid mixture thereof; a liquid petrolatum or a synthetic or semi-synthetic oleaginous liquid fraction, or a mixture thereof; a $C_{16-18}$ aliphatic or branched chain fatty alcohol or fatty acid, or a mixture thereof; glyceryl stearate; xanthan gum; water; and optionally a mixture of a carbomer and triethanolamine, wherein the urea is present in an amount therapeutically effective for treating the fungal condition wherein the urea is present from about 10 to about 60 wt-%.

2. The method of claim 1, wherein the administering step is carried out by topically applying the composition.

3. The method of claim 1, wherein the urea is present from about 30 to about 50 wt-% urea.

4. The method of claim 1, wherein the urea is present from about 10 to about 40 wt-% urea.

5. The method of claim 1, wherein the composition is in a topical form selected from the group consisting of cream, ointment, solution, lacquer, gel, and foam.

6. The method of claim 1, wherein the composition is a gel.

7. The method of claim 1, wherein the urea is present in an amount of about 40 wt-%.

8. The method of claim 7, wherein the composition is a gel or a cream.

* * * * *